(12) United States Patent
Schulz

(10) Patent No.: US 12,215,072 B2
(45) Date of Patent: *Feb. 4, 2025

(54) METHOD AND SYSTEM FOR THE SYNTHESIS OF METHANOL

(71) Applicants: GASCONTEC GMBH, Bad Homburg v. d. Höhe (DE); thyssenkrupp Uhde GmbH, Dortmund (DE)

(72) Inventor: Alexander Schulz, Frankfurt (DE)

(73) Assignees: GASCONTEC GMBH, Bad Homburg V. D. Höhe (DE); THYSSENKRUPP UHDE GMBH, Dortmund (DE)

( * ) Notice: Subject to any disclaimer, the term of this patent is extended or adjusted under 35 U.S.C. 154(b) by 78 days.

This patent is subject to a terminal disclaimer.

(21) Appl. No.: 17/613,702

(22) PCT Filed: May 26, 2020

(86) PCT No.: PCT/EP2020/064551
§ 371 (c)(1),
(2) Date: Nov. 23, 2021

(87) PCT Pub. No.: WO2020/239754
PCT Pub. Date: Dec. 3, 2020

(65) Prior Publication Data
US 2022/0220052 A1    Jul. 14, 2022

(30) Foreign Application Priority Data

May 28, 2019  (EP) .................................... 19177102
Jun. 13, 2019  (EP) .................................... 19180022

(51) Int. Cl.
*C07C 29/152*    (2006.01)
*B01J 19/24*     (2006.01)

(52) U.S. Cl.
CPC ......... *C07C 29/152* (2013.01); *B01J 19/2465* (2013.01)

(58) Field of Classification Search
CPC .................. C07C 29/152; C07C 29/80; C01B 2203/0244; C01B 2203/025;
(Continued)

(56) References Cited

FOREIGN PATENT DOCUMENTS

| EP | 2011564 A1 | 1/2009 |
|---|---|---|
| EP | 3205622 A1 | 8/2017 |
| WO | 2005108336 A1 | 11/2005 |

OTHER PUBLICATIONS

International Search Report issued Aug. 21, 2020 re: Application No. PCT/EP2020/064551, pp. 1-2, citing: WO 2005108336 A1, EP 2011564 A1 and EP 3205622 A1.

*Primary Examiner* — Jafar F Parsa
(74) *Attorney, Agent, or Firm* — CANTOR COLBURN LLP

(57) ABSTRACT

A method for the synthesis of methanol, wherein a carbonaceous energy source flow is supplied to a synthesis gas reactor arrangement for obtaining a synthesis gas flow having hydrogen and carbon oxides, wherein the synthesis gas flow is supplied to a thermal recovery apparatus for recovering heat from the synthesis gas flow and then to a synthesis gas compressor for pressure increase. The synthesis gas flow is supplied at least in part to a first reactor stage of a methanol reactor arrangement for partial conversion to methanol, a residual gas flow having unreacted carbon oxides being obtained from the methanol reactor arrangement, which residual gas flow is supplied to a recycling compressor for increasing its pressure, the pressure-increased gas flow being supplied to the methanol reactor arrangement for partial conversion to methanol, a recovery flow from an unreacted residual gas being supplied to the first reactor stage of a hydrogen recovery arrangement to obtain a H-recycling flow. The

16 Claims, 8 Drawing Sheets

(58) Field of Classification Search
CPC .............. C01B 2203/043; C01B 3/382; B01J 19/2465; B01J 4/001; B01J 19/00; B01J 19/0053; B01J 2219/00006
See application file for complete search history.

METHOD AND SYSTEM FOR THE SYNTHESIS OF METHANOL

TECHNICAL FIELD

The disclosure relates to a method for the synthesis of methanol in accordance with the preamble of claim 1 as well as to a plant for the synthesis of methanol in accordance with the preamble of claim 16.

BACKGROUND

Methanol is usually produced in a reactor of a plant for the synthesis of methanol, a synthesis gas stream containing hydrogen and oxides of carbon being fed to the reactor and in which the exothermic reaction for the production of methanol takes place.

Depending on the manner in which the synthesis gas stream is obtained and depending on which energy carrier is used as the basis of the synthesis gas, the proportion of hydrogen in the fresh synthesis gas may be lower than that which is sought. Particularly in order to improve the stoichiometry of the methanol synthesis, it is therefore often appropriate to recover unreacted hydrogen from a residual gas from the reactor and to recycle this hydrogen to the methanol reactor.

For a recycle of this type, the pressure of the recovered hydrogen has to be raised before feeding it to the reactor.

EP 3 205 622 B1 of the prior art, which is the closest prior art to the present disclosure, discloses a plant for the synthesis of methanol. In that plant, a hydrogen stream which is obtained, by PSA, from a residual gas from the methanol synthesis, is fed to the synthesis gas stream. This feed is carried out operationally upstream of the synthesis gas compressor, so that the pressure of the hydrogen from the hydrogen stream is increased together with the synthesis gas by means of the synthesis gas compressor before being fed to the methanol reactor.

The disadvantage with this prior art is that the requirement for compression of the recovered hydrogen as well means that the synthesis gas compressor has to be larger than before and equally, the energy consumption for compression is higher.

SUMMARY

Starting from this prior art, the disclosure improves the known method for the synthesis of methanol of the prior art so that the pressure of the recovered hydrogen can be increased more economically.

In respect of a method for the synthesis of methanol in accordance with the preamble of claim 1, this is achieved by providing the features of the characterizing portion of claim 1. In respect of a plant for the synthesis of methanol in accordance with the preamble of claim 16, this is achieved by providing the features of the characterizing portion of claim 16.

The inventive concept behind the disclosure is that an increase in pressure of the hydrogen extracted from the hydrogen recovery can also be carried out by means of the recycle compressor. This recycle compressor serves to circulate the major portion of the unreacted residual gas through the methanol reactor. Regularly, only a sub-stream of the unreacted residual gas is fed to the hydrogen recovery, because then, regularly, this entire sub-stream—minus the recovered hydrogen—can be discharged as a purge gas. If the recovered hydrogen is then recombined with the remaining unreacted residual gas for the purposes of increasing the pressure by means of the recycle compressor, then under some circumstances, the pressure of this remaining unreacted residual gas has to be dropped, because the hydrogen recovery is also accompanied by a specific pressure drop. However, it has been shown that nevertheless, the displacement of the pressurization of the recovered hydrogen from the synthesis gas compressor to the recycle compressor results in lower costs.

The proposed method serves for the synthesis of methanol. In the proposed method, a carbon-containing energy carrier stream is fed to a synthesis gas reactor arrangement for obtaining a synthesis gas stream with hydrogen and oxides of carbon. The synthesis gas stream therefore contains hydrogen, carbon monoxide and carbon dioxide and can also contain other components, in particular nitrogen and noble gases, for example. The synthesis gas stream may also be described as the fresh gas stream.

In addition, in the proposed method, the synthesis gas stream is fed to a heat recovery device for recovering heat from the synthesis gas stream and thereafter to a synthesis gas compressor for increasing pressure. This synthesis gas compressor may have multiple stages. What is important is that the synthesis gas stream is fed between the heat recovery device and the synthesis gas compressor of another device or of a plurality of other devices. Furthermore, care should be taken that the heat recovery device regularly constitutes only one stage of a heat recovery arrangement with a plurality of heat recovery devices. Put another way, the synthesis gas stream may be fed to only one heat recovery device of several heat recovery devices which are connected together.

In accordance with the proposed method, at least a portion of the pressure-increased synthesis gas stream is fed to a first reactor stage of a methanol reactor arrangement for partial conversion into methanol. Preferably, substantially the entirety of the pressure-increased synthesis gas stream is fed to the first reactor stage. However, it may also be the case that a portion of the synthesis gas stream is diverted upstream. The feature of partial conversion into methanol is based upon the fact that an unconverted residue of educts is discharged from the methanol reactor arrangement, and therefore the conversion is not complete. The methanol reactor arrangement may have several reactor stages or only a single reactor stage. If the methanol reactor arrangement does not have several reactor stages, then the first reactor stage is the only reactor stage of the methanol reactor arrangement. The first reactor stage of the methanol reactor arrangement is that reactor stage of the methanol reactor arrangement to which at least a portion of the synthesis gas stream is fed before it or a remaining residual gas stream is fed to a further reactor stage. The first reactor stage is therefore the operationally first reactor stage of the methanol reactor arrangement. This situation is consistent with the possible description of the synthesis gas stream as a fresh gas stream. Each individual reactor stage of the methanol reactor arrangement can therefore have several individual reactors for methanol synthesis which are operationally parallel to one another.

In the proposed method, a residual gas stream with unreacted oxides of carbon is obtained from the methanol reactor arrangement, the residual gas stream being fed to a recycle compressor for increasing the pressure of the residual gas stream. The residual gas stream may also contain unreacted hydrogen. If the methanol reactor arrangement has more than one reactor stage, then this residual gas stream may be obtained after any reactor stage. The term "unreacted substance" as used here and below should be understood to mean a substance which has been sent as an educt for methanol synthesis to a reactor stage of the methanol reactor arrangement, in particular to the first reactor stage, and which then leaves the reactor stage without having participated in a reaction for the synthesis of methanol.

Furthermore, the proposed method provides that the pressure-increased residual gas stream is fed to the methanol reactor arrangement for partial conversion into methanol. Thus, this concerns a recycle of the now pressure-increased residual gas stream to the methanol reactor arrangement from which the residual gas stream has in fact been obtained.

In addition, the proposed method provides that a recovery stream formed by an unreacted residual gas of the first reactor stage is fed to a hydrogen recovery arrangement for obtaining a H recycle stream. In the case of an unreacted residual gas, this may mean that this is only a portion of the whole of the unreacted gas from the first reactor stage. The recovery stream may be obtained from the unreacted residual gas by diversion, for example.

The proposed method provides that the H recycle stream has unreacted hydrogen from the unreacted residual gas, the unreacted hydrogen of the H recycle stream being fed again to the first reactor stage for at least partial conversion into methanol. It may be the case that the unreacted hydrogen is only a portion of the whole of the unreacted hydrogen from the first reactor stage and/or only a portion of the whole of the unreacted hydrogen from the unreacted residual gas. Feeding the unreacted hydrogen of the H recycle stream afresh to the first reactor stage can in this case be carried out both directly as well as indirectly. In the case of indirect feeding, then, the unreacted hydrogen is then initially fed to other devices.

The proposed method is characterized in that the pressure of at least a portion of the unreacted hydrogen of the H recycle stream from the first reactor stage up to its feed again into the first reactor stage is increased along with the unreacted oxides of carbon by means of the recycle compressor. Put another way, for at least a portion of the unreacted hydrogen in the H recycle stream between the exit of the unreacted hydrogen from the first reactor stage and fresh feeding of this unreacted hydrogen to the first reactor stage, the pressure is increased by means of the recycle compressor. Because—as already stated—the recycle compressor compresses the residual gas stream with unreacted oxides of carbon, then this compression of this unreacted hydrogen takes place by means of the recycle compressor together with the unreacted oxides of carbons. Preferably, the pressure of substantially all of the unreacted hydrogen of the H recycle stream from the first reactor stage up to being fed afresh to the first reactor stage is increased along with the unreacted oxides of carbon by means of the recycle compressor.

In principle, the pressure of the unreacted hydrogen of the H recycle stream or a portion of this hydrogen can be increased several times before being fed afresh to the first reactor stage. Thus, on the one hand, in addition to pressure-increase by means of the recycle compressor, compression may additionally be carried out by means of the synthesis gas compressor. It may be the case that this additional compression concerns only a portion of the unreacted hydrogen. On the other hand, it may also be the case that the unreacted hydrogen or a portion thereof is pressure-increased several times by means of the recycle compressor prior to being fed afresh to the first reactor stage. This may in particular be the case when a recycle is carried out to the input side of the recycle compressor from the outlet side of the recycle compressor.

However, a preferred embodiment of the disclosure is characterized in that the unreacted hydrogen of the H recycle stream is at least partially, preferably substantially completely pressure-increased exactly once from the first reactor stage up to its feed again into the first reactor stage along with the unreacted oxides of carbon by means of the recycle compressor. As a consequence, at least a portion of the unreacted hydrogen of the H recycle stream from the first reactor stage up to its feed again to the first reactor stage is pressure-increased along with the unreacted oxides of carbon solely by means of the recycle compressor. Thus, no pressure-increase occurs by means of another compressor or the like. By this means, superfluous repeated pressurizations are avoided. It should be noted that this requirement for exactly one pressure-increase by means of the recycle compressor concerns only the unreacted hydrogen from the first reactor stage and which is also contained in the H recycle stream and is also preferably only a portion of this unreacted hydrogen. If, therefore—as is regularly the case—unreacted hydrogen is discharged from the first reactor stage which is not contained in the H recycle stream, then it is not necessary for this unreacted hydrogen as well to undergo exactly one pressure-increase by means of the recycle compressor outside the recovery stream. Moreover, it is then also possible to carry out a multiple pressure-increases.

As will be described below, this renewed feed of the unreacted hydrogen to the first reactor stage may be carried out indirectly in a manner such that the hydrogen is fed to the first reactor stage as part of a series of other streams.

In principle, the aforementioned pressure-increase of the unreacted hydrogen could be a pressure-increase by any amount. Preferably, prior to the at least partial conversion into methanol, the unreacted hydrogen is pressure-increased to a pressure which is higher than the pressure of the H recycle stream from the hydrogen recovery arrangement. Similarly, it may be the case that the unreacted hydrogen prior to feeding it afresh to the first reactor stage is pressure-increased to a pressure which is higher than the pressure of the recovery stream upon feeding to the hydrogen recovery arrangement.

The pressure-increase of the unreacted hydrogen can on the one hand be carried out prior to feeding to the hydrogen recovery arrangement. Thus, it may be the case that the recovery stream as a whole is pressure-increased. The pressure-increase of the unreacted hydrogen may, however, also be carried out after feeding to the hydrogen recovery arrangement. Thus, the pressure-increase of the unreacted hydrogen of the H recycle stream may, for example, be carried out by pressure-increasing the H recycle stream as a whole.

The synthesis gas reactor arrangement, the synthesis gas compressor, the methanol reactor arrangement, the heat recovery device, the recycle compressor and the hydrogen recovery arrangement may be comprised in a plant for the synthesis of methanol.

Preferably, the synthesis gas stream obtained from the synthesis gas reactor arrangement has a production pressure which is more than 40 bar, preferably more than 50 bar, in particular more than 60 bar, more particularly more than 70 bar.

A preferred embodiment of the method is characterized in that the pressure-increased synthesis gas stream is at a pressure of more than 60 bar, preferably more than 70 bar, in particular more than 80 bar and more preferably more than 90 bar.

In principle, the residual gas stream which is fed to the recycle compressor may have any composition as long as the residual gas stream comprises unreacted oxides of carbon, generally in any proportion, and the unreacted hydrogen from the recovery stream. Preferably, however, the residual gas stream which is fed to the recycle compressor has a molar proportion of hydrogen of less than 90%, in particular less than 85% and more particularly less than 80%. Alternatively or in addition, the residual gas stream which is fed to the recycle compressor may have a molar proportion of hydrogen of more than 50%, in particular more than 60% and more particularly more than 70%. This molar proportion of hydrogen is with respect to the entire molar proportion of hydrogen of the residual gas stream. This includes not only the unreacted hydrogen from the H recycle stream, but also other hydrogen in the residual gas stream.

Preferably, the methanol reactor arrangement comprises a methanol separation device for obtaining the unreacted residual gas of the first reactor stage and a raw methanol stream from the first reactor stage. In principle, the methanol separation device can function in any manner. In particular, the methanol separation device may comprise a condensation device for obtaining the unreacted residual gas of the first reactor stage and the raw methanol stream from the first reactor stage by condensation.

It may be the case that only a portion of the compressed residual gas stream is fed to the methanol reactor arrangement. In particular and preferably, a portion of the pressure-increased residual gas stream is diverted and fed to the synthesis gas reactor arrangement. In this regard, particularly preferably, the diverted portion of the pressure-increased residual gas stream may be fed to the energy carrier stream.

As already set out, in principle, it may be the case that the methanol reactor arrangement comprises only a single methanol reactor stage. A further preferred embodiment of the method is characterized in that the methanol reactor arrangement has a plurality of reactor stages for the synthesis of methanol which are operationally connected in series. In this regard, each individual reactor stage can have one or more reactors. In this regard, the reactors of a reactor stage can in particular be operationally connected together in parallel. Furthermore, it may be the case that a respective unreacted residual gas is obtained from each of the plurality of reactor stages by means of the methanol separation device.

The fact that the reactor stages are operationally connected in series means that residual gas from one reactor stage—as long as it not the last reactor stage in the series of reactor stages—is fed directly or indirectly to the respectively adjacent downstream reactor stage. In principle, the above recycle compressor can be configured in any manner with respect to the plurality of reactor stages. In a variation, the recycle compressor is operationally connected between two reactor stages. This means that at least a portion of the unreacted residual gas from a reactor stage is fed to the recycle compressor as the residual gas stream and the pressure-increased residual gas stream is then fed to the reactor stage which is disposed downstream of this reactor stage.

In principle, the H recycle stream can go anywhere, as long as at least a portion of its hydrogen is converted into methanol. In accordance with a further preferred embodiment of the method, in this regard, it is preferable for the H recycle stream to be fed to the unreacted residual gas from a reactor stage which is operationally downstream of the first reactor stage. In other words, the unreacted hydrogen of the H recycle stream is treated after feeding it together with at least a portion of the unreacted residual gas to a reactor stage other than the first reactor stage. In this manner, the H recycle stream "by-passes" one or more reactor stages after the first reactor stage. The advantage of a strategy of this type is that in this manner, the pressure drop of the H recycle stream because of the hydrogen recovery is basically parallel to the pressure drop of the unreacted residual gas of the downstream reactor stage in this reactor stage. Put another way, the respective pressures of this unreacted residual gas and of the H recycle stream are closer to each other, which in turn reduces a pressure drop generated upon combination by equilibrating to the lower pressure level.

Preferably, the H recycle stream is fed to the recycle compressor together with the residual gas stream for increasing the pressure.

In accordance with a preferred embodiment of the method, the residual gas stream is obtained from a reactor stage which is operationally downstream of the first reactor stage. In other words, the residual gas stream fed to the recycle compressor does not originate from the first reactor stage—i.e. the reactor stage to which at least a portion of the synthesis gas stream is fed directly—but to a downstream reactor stage. Furthermore, the pressure-increased residual gas stream from the first reactor stage may be fed to the recycle compressor. In principle, the pressure-increased residual gas stream may, however, be fed to another reactor stage of the plurality of reactor stages. Similarly, it may be the case that the pressure-increased residual gas stream is divided and fed to several reactor stages of the plurality of reactor stages.

A further preferred embodiment of the proposed method is characterized in that the residual gas stream is obtained from a reactor stage of the plurality of reactor stages which is in the last operational position. This and the preceding variations mean that the necessary pressure drops brought about by combining the streams are reduced.

In principle, the recovery stream can be obtained at any position and from any origin within the methanol reactor arrangement. The recovery stream contains unreacted hydrogen from an unreacted residual gas of the first reactor stage. In a first preferred variation, at least a portion of the recovery stream is diverted from the unreacted residual gas of the first reactor stage. it may be the case that at least a portion of the recovery stream is diverted operationally upstream of the recycle compressor.

It may also be the case, however, that the pressure of the recovery stream has already been increased by means of the recycle compressor. Thus, a further preferred embodiment of the method is characterized in that the recovery stream is fed to the hydrogen recovery arrangement at a feed pressure which is higher than a residual gas pressure at which the residual gas stream is obtained from the methanol reactor arrangement. A preferred possibility for increasing the pressure of the recovery stream is to compress it first by means of the recycle compressor. Accordingly, it is preferable for at least a portion of the recovery stream to be diverted out of the residual gas stream operationally downstream of the recycle compressor.

It may also be the case, however, that more than one stream is fed to the hydrogen recovery arrangement, from which hydrogen is obtained. In accordance with a preferred embodiment of the method, for example, at least a portion of the synthesis gas stream which in particular has been pressure-increased is diverted for feeding to a water gas shift reaction device. It may also be the case that the synthesis gas stream which has preferably been pressure-increased is fed in its entirety to the water gas shift reaction device. It is also preferable for at least a portion of a further recovery stream to be obtained from the water gas shift reaction device and be fed to the hydrogen recovery arrangement for obtaining the H recycle stream. In other words, at least a portion of the hydrogen from the H recycle stream is obtained from this further recovery stream. This water gas shift reaction device may be included in the arrangement for the synthesis of methanol.

In particular, at least a portion of the oxides of carbon in the synthesis gas stream which in particular has been pressure-increased can react to form carbon dioxide and hydrogen in the water gas shift reaction device by means of a water gas shift reaction. Thus, by increasing the proportion of hydrogen, the stoichiometry of the methanol synthesis can be improved.

Similarly, it may generally be the case that the H recycle stream is not initially fed to the first reactor stage. In contrast, in accordance with a further preferred embodiment of the method, the H recycle stream is fed to the synthesis gas stream which in particular has been pressure-increased. This in particular means that the H recycle stream is fed to the synthesis gas stream operationally downstream of the synthesis gas reactor arrangement. Preferably, the H recycle stream is fed to the synthesis gas stream operationally downstream of the synthesis gas compressor. Put another way, the H recycle stream is fed to the synthesis gas stream operationally upstream of the first reactor stage. By feeding the synthesis gas stream to the first reactor stage of the methanol reactor arrangement, as a result, the hydrogen of the H recycle stream is fed again to the first reactor stage.

In addition to a reactor for the production of the synthesis gas, the synthesis gas reactor arrangement may have further devices. Thus, the synthesis gas reactor arrangement may have a device for desulphurization of the carbon-containing energy carrier stream, a saturation stage for saturating the carbon-containing energy carrier stream with water, a pre-reformer for pre-reforming the carbon-containing energy carrier stream and/or a device for heating the carbon-containing energy carrier stream, respectively operationally upstream of the reactor.

In principle, the synthesis gas stream may be obtained from the energy carrier stream in any manner. Preferably, for obtaining the synthesis gas stream, an oxygen-containing stream is fed to the synthesis gas reactor arrangement. In principle, the oxygen-containing stream may contain other components in addition to the oxygen. Thus, the oxygen-containing stream may also be ambient air.

In principle, the synthesis gas stream may be obtained by steam reforming the carbon-containing energy carrier stream. A further preferred embodiment of the method is characterized in that in the synthesis gas reactor arrangement, the synthesis gas stream is obtained by means of autothermal reforming of the carbon-containing energy carrier stream. In the case of autothermal reforming of this type, a catalytic partial oxidation is suitable for the heat required for the endothermic reforming reaction. In contrast to pure steam reforming, autothermal reforming offers the advantage that a synthesis gas stream can be provided which is at a higher pressure. Alternatively or in addition, the synthesis gas stream may be obtained in the synthesis gas reactor arrangement by means of a partial oxidation of the carbon-containing energy carrier stream.

In principle, autothermal reforming may also be operated using ambient air. However, preferably, the oxygen-containing stream is obtained from an air separation device for obtaining a stream of oxygen from ambient air. Furthermore, the air separation device may also be configured to obtain a stream of nitrogen. In particular, it may then be the case that the oxygen-containing stream substantially consists of oxygen. In this manner, the proportion of inert gases in the methanol synthesis is reduced, so that the dimensions of various devices in the plant can be smaller. Preferably, the plant for the synthesis of methanol includes the air separation device.

In accordance with a preferred embodiment of the method, the H recycle stream is fed to the energy carrier stream. In particular, the H recycle stream may be fed to the energy carrier stream operationally upstream of the synthesis gas reactor arrangement.

In addition to the H recycle stream, the hydrogen recovery arrangement may also output other streams. Preferably, the hydrogen recovery arrangement outputs a purge. This can in particular be discharged for combustion.

In principle, the H recycle stream may have any composition, as long as it contains the unreacted hydrogen from the unreacted residual gas of the first reactor stage. In accordance with a further preferred embodiment of the method, the H recycle stream has a higher molar proportion of hydrogen than the recovery stream. This is not in respect of the unreacted hydrogen from the unreacted residual gas of the first reactor stage, but in respect of the hydrogen in the H recycle stream as a whole. In other words, the hydrogen in the H recycle stream is concentrated compared with the recovery stream. Similarly, it is preferable for the H recycle stream to have a higher molar proportion of hydrogen than the purge.

In principle, the hydrogen recovery arrangement can function in accordance with any principle, for example based on a membrane or a cooling device. A preferred embodiment of the method is characterized in that the hydrogen recovery arrangement has a pressure swing adsorption device (PSA) for obtaining the H recycle stream from the recovery stream. In this manner, a high rate of recovery of hydrogen in the H recycle stream can be obtained. Similarly, the pressure drops in such a pressure swing adsorption device are still acceptable. A high degree of purity of the hydrogen is therefore in principle not a requirement, but may be obtained. It may therefore be the case that the H recycle stream substantially consists of hydrogen.

The proposed plant serves for the synthesis of methanol. It has a synthesis gas reactor arrangement for obtaining a synthesis gas stream with hydrogen and oxides of carbon from a carbon-containing energy carrier stream, a synthesis gas compressor for pressure-increasing the synthesis gas stream, a methanol reactor arrangement which has a first reactor stage, a heat recovery device for recovering heat from the synthesis gas stream, a hydrogen recovery arrangement and a recycle compressor.

In the proposed plant, at least a portion of the pressure-increased synthesis gas stream is fed to the first reactor stage for partial conversion into methanol.

Furthermore, in the proposed plant, a residual gas stream with unreacted oxides of carbon is obtained from the methanol reactor arrangement, the residual gas stream being fed to the recycle compressor for increasing the pressure of the residual gas stream, wherein the pressure-increased residual gas stream is fed to the methanol reactor arrangement for partial conversion into methanol, the synthesis gas stream is fed to the heat recovery device and thereafter to the synthesis gas compressor, wherein a recovery stream formed by an unreacted residual gas of the first reactor stage is fed to the hydrogen recovery arrangement for obtaining a H recycle stream, the H recycle stream having unreacted hydrogen from the unreacted residual gas, and the unreacted hydrogen of the H recycle stream being fed again to the first reactor stage for at least partial conversion into methanol.

The proposed plant is characterized in that the pressure of at least a portion of the unreacted hydrogen of the H recycle stream from the first reactor stage up to its feed again into the first reactor stage is increased along with the unreacted oxides of carbon by means of the recycle compressor.

Features, advantages and properties of the proposed plant correspond to the features, advantages and properties of the proposed method, and vice versa.

BRIEF DESCRIPTION OF THE DRAWINGS

Further details, features, targets and advantages of the present disclosure will now be described with the aid of the drawings which are given by way of exemplary embodiment. In the drawings.

DETAILED DESCRIPTION OF THE DRAWINGS

Figure 1:
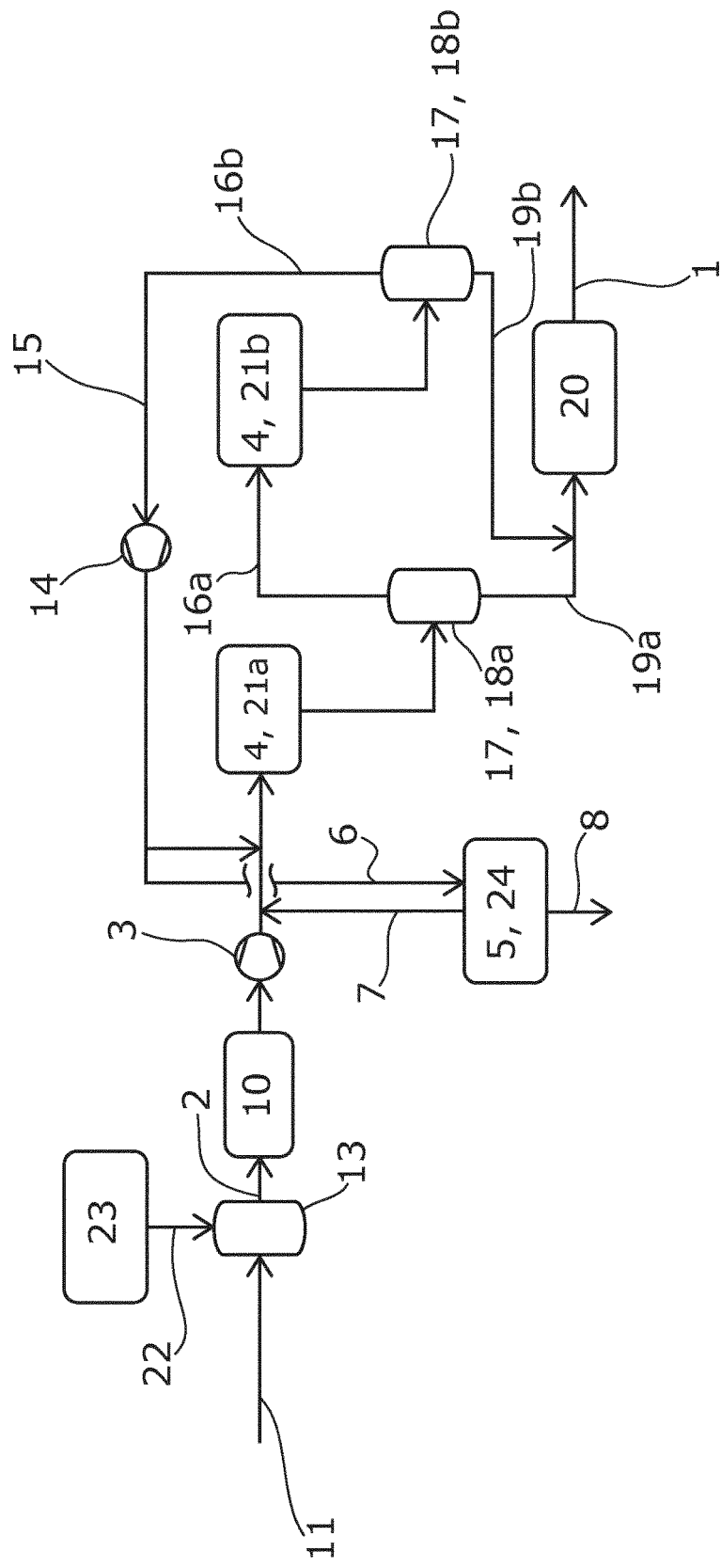
FIG. 1 diagrammatically shows the flow diagram for a plant for carrying out the proposed method in accordance with a first exemplary embodiment, FIG. 2 diagrammatically shows the flow diagram for a plant for carrying out the proposed method in accordance with a second exemplary embodiment, FIG. 3 diagrammatically shows the flow diagram for a plant for carrying out the proposed method in accordance with a third exemplary embodiment, FIG. 4 diagrammatically shows the flow diagram for a plant for carrying out the proposed method in accordance with a fourth exemplary embodiment, FIG. 5 diagrammatically shows the flow diagram for a plant for carrying out the proposed method in accordance with a fifth exemplary embodiment, FIG. 6 diagrammatically shows the flow diagram for a plant for carrying out the proposed method in accordance with a sixth exemplary embodiment, FIG. 7 diagrammatically shows the flow diagram for a plant for carrying out the proposed method in accordance with a seventh exemplary embodiment, and FIG. 8 diagrammatically shows the flow diagram for a plant for carrying out the proposed method in accordance with an eighth exemplary embodiment.

The plant shown in FIG. 1 in accordance with a first exemplary embodiment of the proposed plant is for the synthesis of methanol 1 and can be operated in accordance with the proposed method.

A synthesis gas stream 2 which substantially consists of hydrogen, carbon monoxide and carbon dioxide is obtained from an energy carrier stream 11 which is formed by natural gas and which is therefore carbon-containing, and which is fed to a synthesis gas reactor arrangement 13. In the synthesis gas reactor arrangement 13, autothermal reforming takes place in order to obtain the synthesis gas stream 2. For autothermal reforming, an oxygen-containing stream 22 is supplied which in this case has been obtained from an air separation device 23 and which substantially consists of oxygen. The air separation device 23 in this case is configured to obtain a stream of oxygen—i.e. in this case the oxygen-containing stream 22—from the ambient air. The synthesis gas stream 2 is obtained at a production pressure which is substantially 60 bar. The synthesis gas stream 2 is initially fed to a heat recovery arrangement 10 in which the synthesis gas stream 2 is cooled and in this manner, a portion of the heat produced during autothermal reforming is recovered. Next, the synthesis gas stream 2 is fed to a synthesis gas compressor 3 of the plant for further pressure-increased.

Next, the synthesis gas stream is fed to the first reactor stage 21a of a methanol reactor arrangement 4, in which reactor stage 21a, synthesis of methanol takes place and at least a portion of the synthesis gas stream 2 is converted into methanol 1. The methanol synthesis takes place at a synthesis pressure of more than 60 bar, and in particular at a synthesis pressure of substantially 80 bar.

The plant has a hydrogen recovery arrangement 5 configured as a pressure swing adsorption device 24—which can also be termed a PSA—wherein a H recycle stream 7 is obtained from a recovery stream 6, which H recycle stream 7 substantially consists of hydrogen. In addition, the remaining gas is discharged from the hydrogen recovery arrangement 5 as a purge 8 and is then burned in a fired heating device of the plant (not shown here). The H recycle stream 7 is fed to the synthesis gas stream 2.

As can be seen in FIG. 1, the plant of the first exemplary embodiment also has a recycle compressor 14 which compresses a residual gas stream 15. The residual gas stream 15 has unreacted residual gas 16b which in turn has substantially those components of the synthesis gas which have not been converted into methanol 1 in the methanol reactor arrangement 4. Accordingly, the residual gas stream 15 contains unreacted oxides of carbon in particular. The residual gas stream 15 which has been pressure-increased in this manner is fed afresh to a first portion of the methanol reactor arrangement 4.

The unreacted residual gas 16a, b is obtained from a methanol separation device 17 of the methanol reactor arrangement 4, which in this case comprises two condensation devices 18a, b. By means of condensation, they respectively produce the unreacted residual gas 16a, b on the one hand and a respective raw methanol stream 19a, b on the other hand. The raw methanol streams 19a, b are then fed into a distillation step 20 of the plant so that methanol 1 can be obtained from the raw methanol streams 19a, b.

In the plant of the exemplary embodiment of FIG. 1, the methanol reactor arrangement 4 has two reactor stages 21a, b for methanol synthesis which are operationally connected in series. In this exemplary embodiment, the first reactor stage 21a has two isothermal reactors which are disposed in parallel and the second reactor stage 21b has a single isothermal reactor. In this regard, each of the two condensation devices 18a, b is fed by the product stream from each of the reactor stages 21a, b. In this regard, that reactor stage 21a to which the synthesis gas stream 2 is fed directly is described as the first reactor stage 21a. The reactor stage 21b is then that which is operationally downstream such that it is fed by the unreacted residual gas 16a from the first reactor stage 21a for conversion into methanol 1.

In this exemplary embodiment of FIG. 1, the recovery stream 6 is diverted from the residual gas stream 15 which has been pressure-increased by means of the recycle compressor. This residual gas stream 15 which is fed to the recycle compressor 14 is not obtained from the unreacted residual gas 16a of the first reactor stage 21a, but from the unreacted residual gas 16b of the reactor stage which is operationally downstream of the first reactor stage 21a and is therefore termed the second reactor stage 21b.

Similarly, this residual gas stream 15 also contains unreacted hydrogen from the first reactor stage 21a in addition to the unreacted oxides of carbon which have already been mentioned. Any unreacted hydrogen from the residual gas 16a of the first reactor stage 21a is fed to the second reactor stage 21b. Because a complete reaction of the hydrogen also does not take place in the second reactor stage 21b, the unreacted residual gas 16b of the second reactor stage 21b also contains unreacted hydrogen from the first reactor stage 21a.

Because the recovery stream 6 is diverted from the pressure-increased residual gas stream 15, the H recycle stream 7 also contains unreacted hydrogen from the unreacted residual gas 16a of the first reactor stage 21a. In particular, a second portion of the pressure-increased residual gas stream 15 is diverted as the recovery stream 6. Because the H recycle stream 7 is fed to the pressure-increased synthesis gas stream 2, the unreacted hydrogen from the residual gas 16a of the first reactor stage 21a in the recovery stream 6—and therefore also from the H recycle stream 7—is fed to this first reactor stage 21 again for conversion into methanol. Between leaving the first reactor stage 21a and being fed again to the first reactor stage 21a, however, as a component of the residual gas stream 15, the unreacted hydrogen of the H recycle stream 7 has undergone pressure-increase by means of the recycle compressor 14, and in fact exactly once and together with the unreacted oxides of carbon in the residual gas stream 15. Since the H recycle stream 7 is fed to the synthesis gas stream 2 operationally downstream of the synthesis gas compressor 3, then pressure-increase of the hydrogen in the H recycle stream 7 does not take place. The residual gas stream 15 which is compressed by means of the recycle compressor 14 is then fed directly again to the aforementioned first portion of the first reactor stage 21a.

Figure 2:
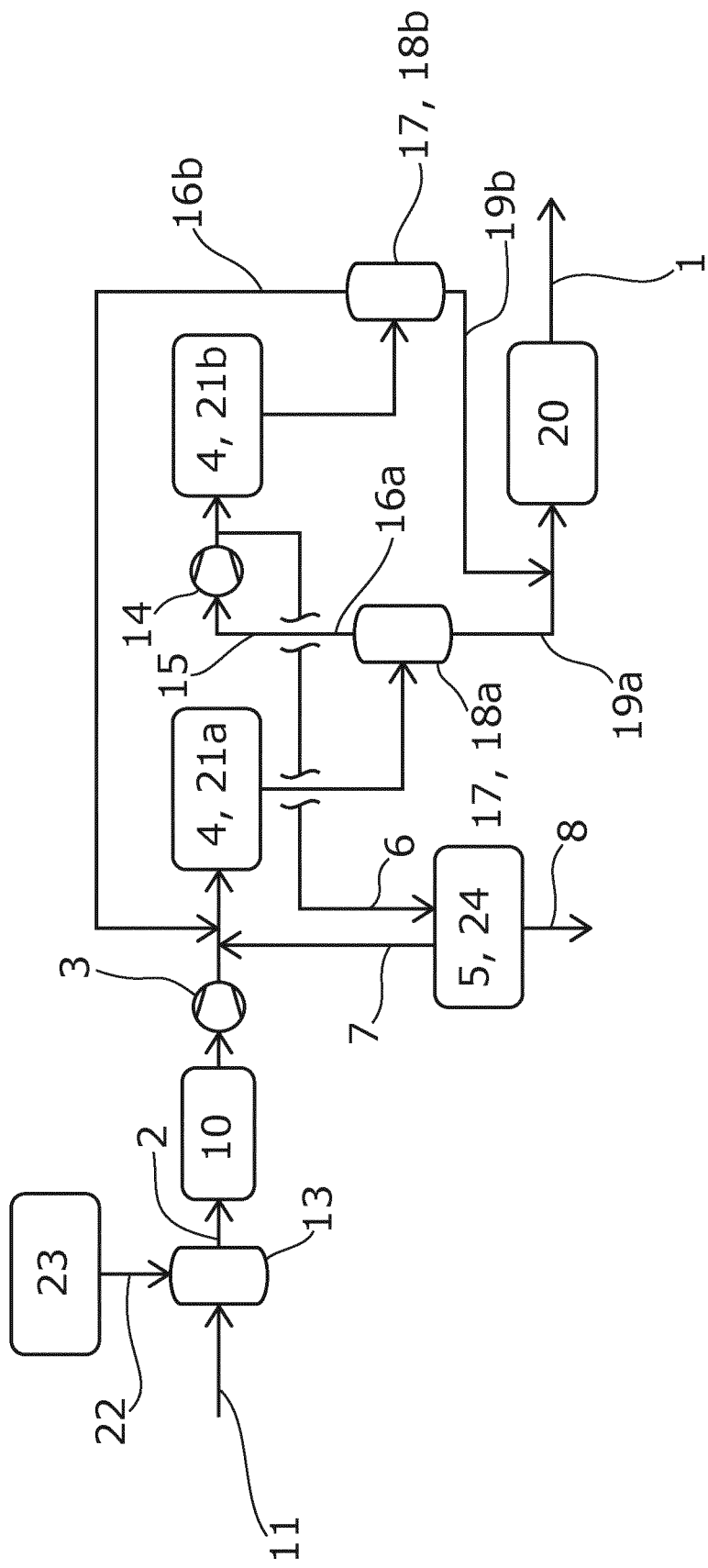

The second exemplary embodiment of the proposed plant, shown in FIG. 2, differs from the exemplary embodiment shown in FIG. 1 in that the recycle compressor 14 is operationally disposed between the first reactor stage 21a and the reactor stage 21b which is downstream of the former. As a consequence, the residual gas stream 15 which is fed to the recycle compressor 14 is obtained from the unreacted residual gas 16a of the first reactor stage 21a. The residual gas stream 15 which is compressed by means of the recycle compressor 14 along with the unreacted oxides of carbon is fed to the reactor stage 21b which is downstream of the first reactor stage 21a. The unreacted residual gas 16b from this reactor stage 21b is fed back to the first reactor stage 21a without further compression. In contrast to that shown in the first exemplary embodiment, the recovery stream 6 is obtained from the unreacted residual gas 16a of the first reactor stage 21a, wherein in addition, in agreement with the first exemplary embodiment, diversion of the recovery stream 6 is carried out operationally downstream of the recycle compressor 14. As a consequence, in the second exemplary embodiment as well, pressure-increased of the unreacted hydrogen from the residual gas 16a of the first reactor stage 21a in the H recycle stream 7 takes place exactly once along with the unreacted oxides of carbon occurs by means of the recycle compressor 14, before this unreacted hydrogen is fed to the first reactor stage 21a again.

Figure 3:
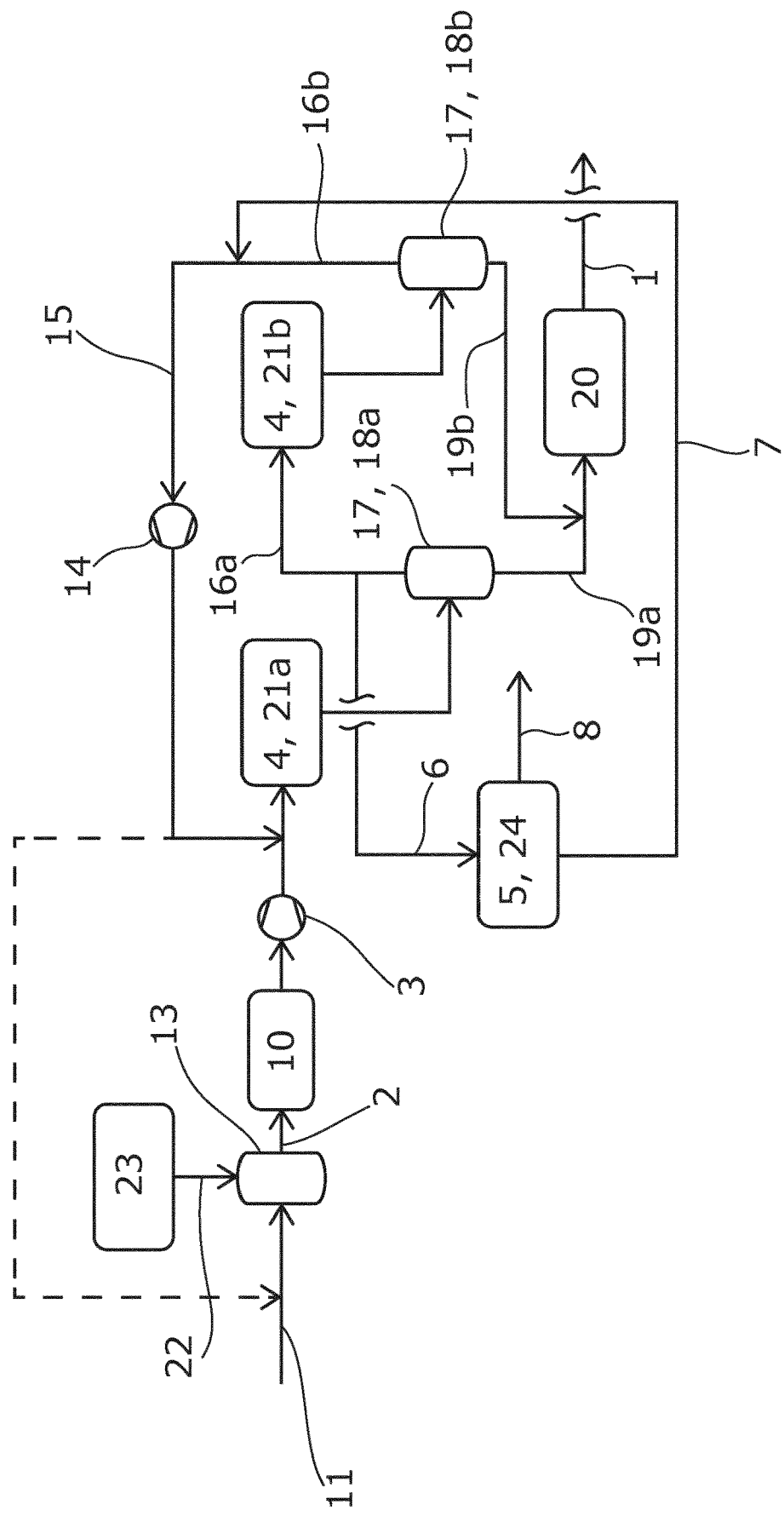

In the third exemplary embodiment of FIG. 3, in similar manner to the second exemplary embodiment, the recovery stream 6 is obtained from the residual gas 16a of the first reactor stage 21a. In contrast to the second exemplary embodiment, however, there is no recycle compressor 14 between the first reactor stage 21a and the second reactor stage 21b. Moreover, the recycle compressor 14 is disposed operationally downstream of the second reactor stage 21b, as was the case with the first exemplary embodiment.

In contrast to both the first exemplary embodiment and the second exemplary embodiment, in the third exemplary embodiment, the H recycle stream 7 is fed to the residual gas 16b of the second reactor stage 21b which is downstream of the first reactor stage 21a. In particular, this feed takes place before the pressure-increase by means of the recycle compressor 14. In this manner, the hydrogen in the H recycle stream 7 corresponding to the unreacted hydrogen from the residual gas 16a of the first reactor stage 21a is pressure-increased, by means of the recycle compressor 14, in the recovery stream 6 along with the remaining unreacted residual gas 16b of the second reactor stage 21b and in particular along with unreacted oxides of carbon. This pressure-increase is carried out before this unreacted hydrogen is fed to the first reactor stage 21a again, which compensates for the lack of pressure-increase due to the missing synthesis gas compressor.

In addition, in the third exemplary embodiment, a portion of the pressure-increased residual gas stream 15 is diverted and fed to the energy carrier stream 11. This diverted portion of the pressure-increased residual gas stream 15 undergoes a further pressure-increase by means of the synthesis gas compressor 2. For the non-diverted portion of the residual gas stream 15, a pressure-increase by means of the recycle compressor 14 has been carried out exactly once. However, it is also possible to dispense with this diversion of a portion of the pressure-increased residual gas stream 15.

Figure 4:
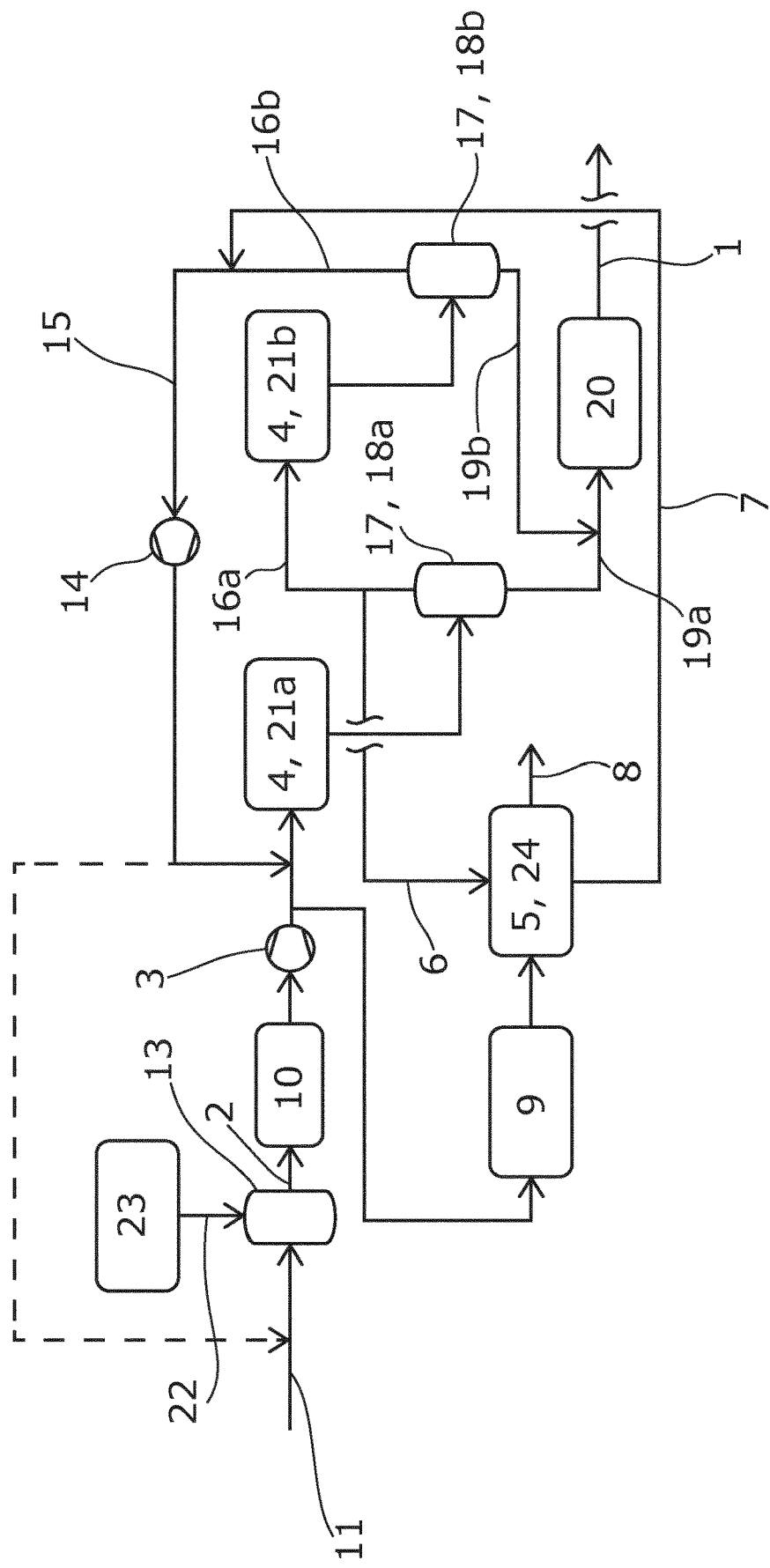

The plant in accordance with the fourth exemplary embodiment of FIG. 4 corresponds to the third exemplary embodiment of FIG. 3. However, it includes a water gas shift reaction device 9 to which a portion of the pressure-increased synthesis gas stream 2 is fed. The water gas shift reaction which occurs in the water gas shift reaction device 9 results in raising the proportion of hydrogen in the diverted portion of the pressure-increased synthesis gas stream 2. In this case, the portion of the synthesis gas stream 2 from the water gas shift reaction device 9 which has been diverted in this manner and which has undergone the water gas shift reaction forms a further recovery stream which is fed to the hydrogen recovery arrangement 5 together with the recovery stream 6. In the same manner as in the exemplary embodiment of FIG. 3, the H recycle stream 7 is fed to the residual gas 16b of the second reactor stage 21b which is downstream of the first reactor stage 21a, so that therefore, even with this exemplary embodiment, pressure-increase is carried out by means of the recycle compressor 14 along with the unreacted oxides of carbon.

Figure 5:
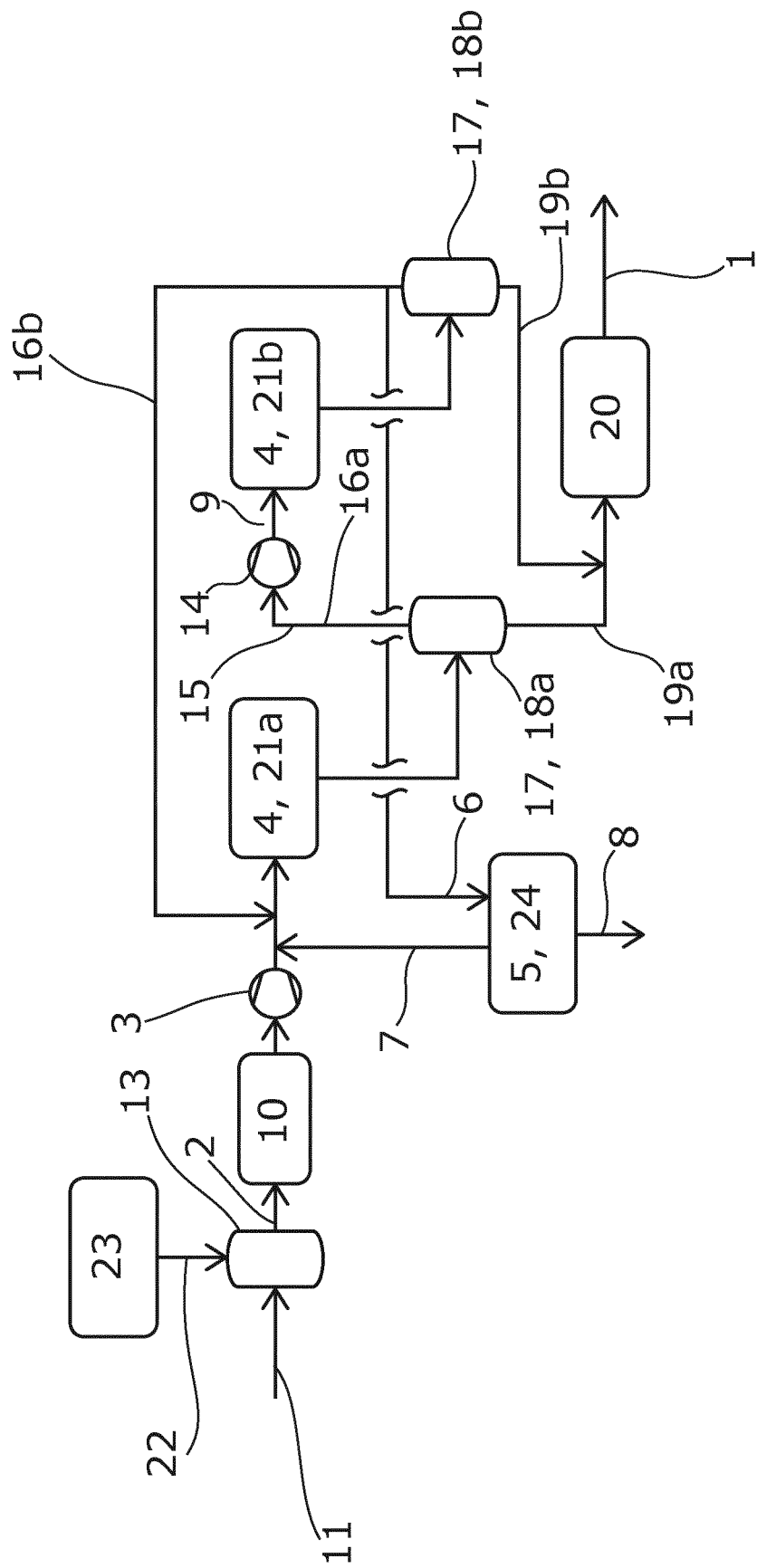

The fifth exemplary embodiment of FIG. 5 disposes the recycle compressor 14 between the reactor stages 21a, b of the methanol reactor arrangement 4, in similar manner to that of the second exemplary embodiment on which the fifth exemplary embodiment is also based. In contrast to the second exemplary embodiment, the recovery stream 6 is obtained from the residual gas 16b from the second reactor stage 21b. In this manner, the pressure of the hydrogen in this recovery stream 6 and therefore also in the H recycle stream 7 is increased by means of the recycle compressor 14, and in fact in particular before being fed to the second reactor stage 21b.

Figure 6:
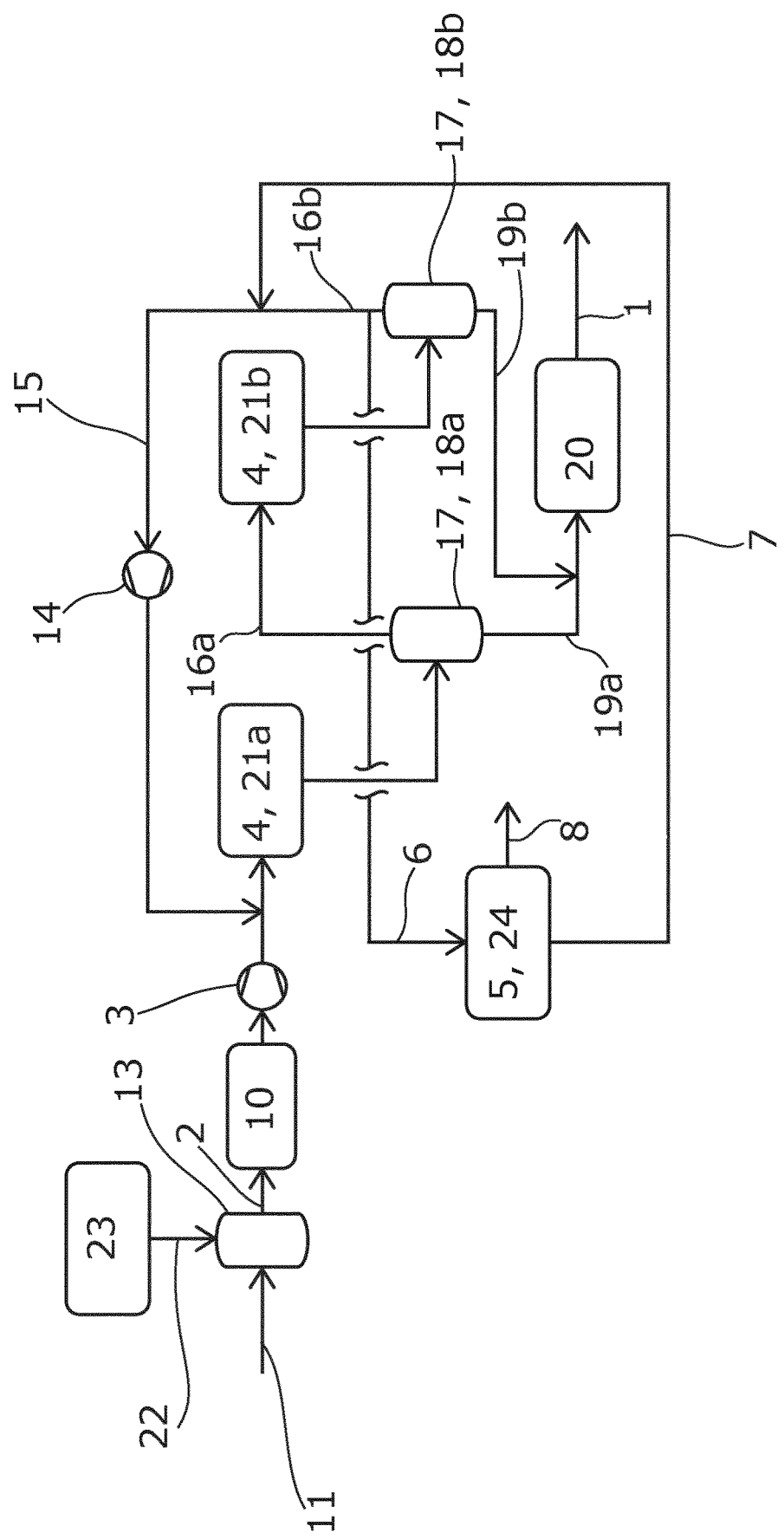

The sixth exemplary embodiment of FIG. 6 is in principle based on the first exemplary embodiment of FIG. 1. In contrast to the latter, and in fact in similar manner to the fifth exemplary embodiment of FIG. 5, the recovery stream 6 is obtained from the unreacted residual gas 16b of the second reactor stage 21b. Another distinction from the first exemplary embodiment of FIG. 1 and in similar manner to the third and fourth exemplary embodiments of FIGS. 3 and 4, the H recycle stream 7 is recycled to the residual gas 16b of the second reactor stage 21b which is downstream of the first reactor stage 21a. This infeed is operationally downstream of the diversion for the recovery stream 6.

Figure 7:
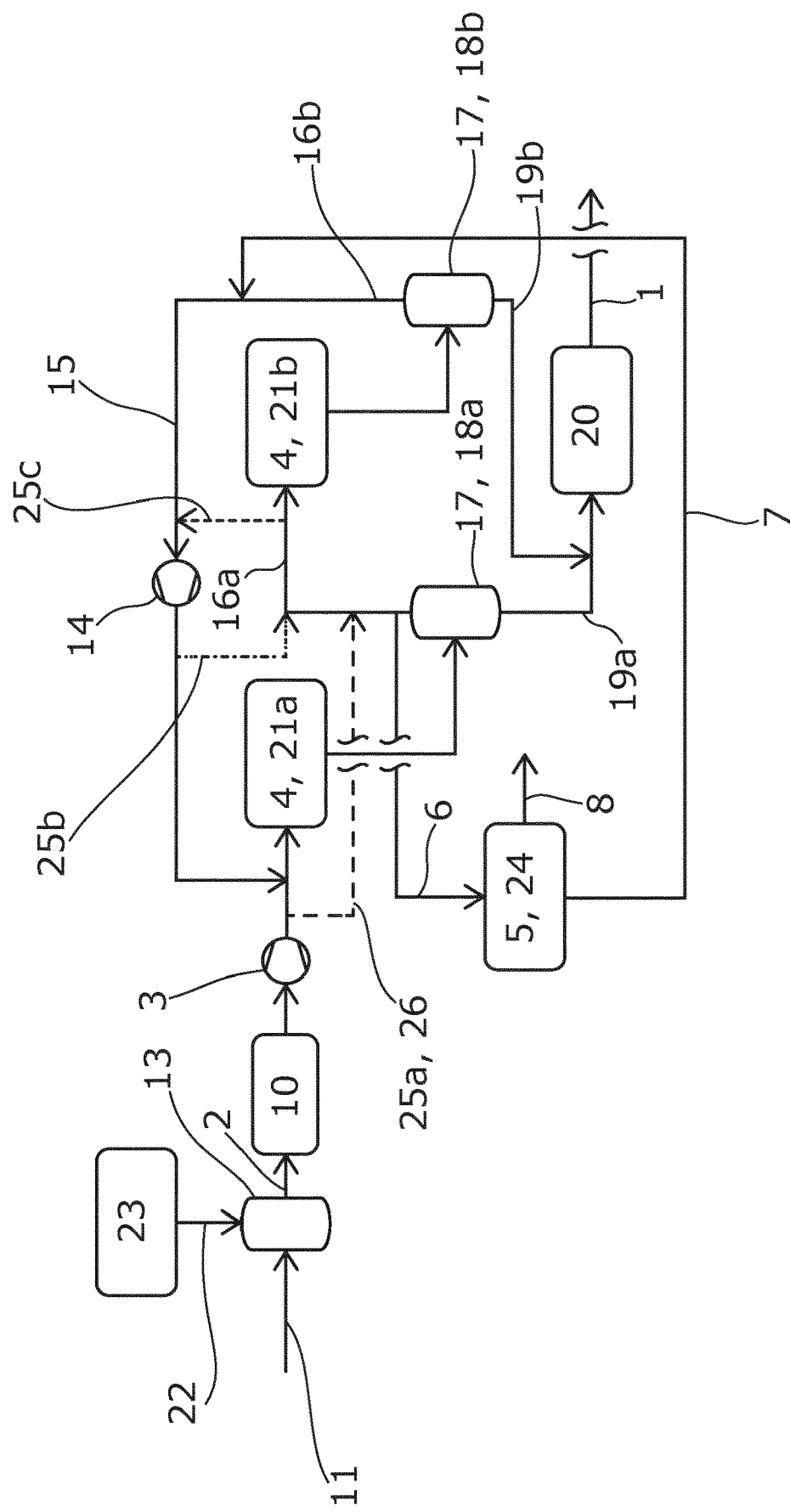

The seventh exemplary embodiment of FIG. 7 is based initially on the third exemplary embodiment of FIG. 3, but without the diversion of a portion of the pressure-increased residual gas stream 15 to the energy carrier stream 11. The seventh exemplary embodiment shows three respectively alternative ways of connecting compared with the third exemplary embodiment. In this context, the seventh exemplary embodiment includes three subsidiary exemplary embodiments.

The first variation proposes a first bypass stream 25a which branches from the pressure-increased synthesis gas stream 2 and is fed to the unreacted residual gas 16a of the first reactor stage 21a. The feed to the unreacted residual gas 16a of the first reactor stage 21a is carried out operationally downstream of the diversion of the recovery stream 6. Thus, in this manner, a portion of the synthesis gas stream 2 is diverted in order to form a further synthesis gas stream 26 which corresponds to the first bypass stream 25a and which bypasses the first reactor stage 21a. In accordance with the layout of FIG. 7, this diversion is operationally upstream of the feed of the pressure-increased residual gas stream 15. However, it would also be possible to envisage this diversion being made operationally downstream of the feed for the pressure-increased residual gas stream 15.

The second variation, which is an alternative to the first variation, proposes a second bypass stream 25b which branches off from the pressure-increased residual gas stream 15 and which is fed to the unreacted residual gas 16a of the first reactor stage 21a, and in fact is again downstream of the diversion for the recovery stream 6. In this manner, then, partial by-passing of the first reactor stage 21a occurs by means of the pressure-increased residual gas stream 15.

The third variation, which is an alternative to the first two variations, proposes a third bypass stream 25c which is operationally downstream of the diversion for the recovery stream 6 from the unreacted residual gas 16a of the first reactor stage 21a and which is fed to the residual gas stream 15 prior to pressure-increase. In this manner, therefore, a portion of the unreacted residual gas 16a of the first reactor stage 21a initially by-passes the second reactor stage 21b.

Figure 8:
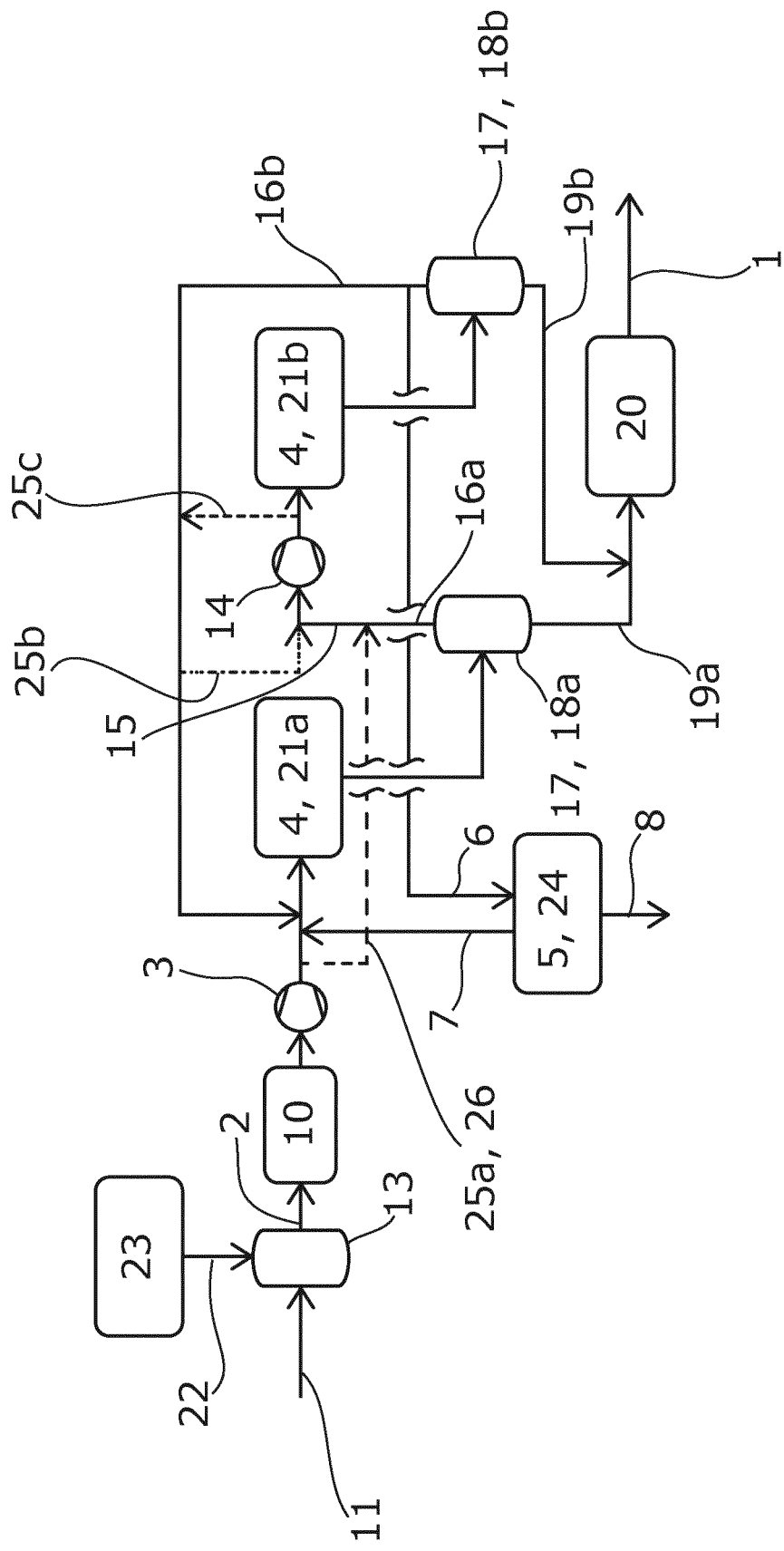

The eighth exemplary embodiment of FIG. 8 is based on the fifth exemplary embodiment of FIG. 5 and also respectively shows three alternative connection variations, in this case with respect to the fifth exemplary embodiment. These three connection variations correspond to connection variations of the seventh exemplary embodiment of FIG. 7 with the bypass streams 25a, 25b, 25c.

The invention claimed is:

1. A method for the synthesis of methanol, wherein a carbon-containing energy carrier stream is fed to a synthesis gas reactor arrangement for obtaining a synthesis gas stream with hydrogen and oxides of carbon, wherein the synthesis gas stream is fed to a heat recovery device for recovering heat from the synthesis gas stream and thereafter to a synthesis gas compressor for increasing pressure, wherein at least a portion of the pressure-increased synthesis gas stream is fed to a first reactor stage of a methanol reactor arrangement for partial conversion into methanol, wherein a residual gas stream with unreacted oxides of carbon is obtained from the methanol reactor arrangement, the residual gas stream being fed to a recycle compressor for increasing the pressure of the residual gas stream, wherein the pressure-increased residual gas stream is fed to the methanol reactor arrangement for partial conversion into methanol, wherein a recovery stream from an unreacted residual gas from the first reactor stage is fed to a hydrogen recovery arrangement for obtaining a H recycle stream, the H recycle stream having unreacted hydrogen from the unreacted residual gas, the unreacted hydrogen of the H recycle stream being fed again to the first reactor stage for at least partial conversion into methanol, wherein the pressure of at least a portion of the unreacted hydrogen of the H recycle stream from the first reactor stage up to its feed again into the first reactor stage is increased along with the unreacted oxides of carbon by means of the recycle compressor.

2. The method according to claim 1, wherein the methanol reactor arrangement comprises a methanol separation device for obtaining the unreacted residual gas from the first reactor stage and a raw methanol stream from the first reactor stage, wherein the methanol separation device comprises a condensation device for obtaining the unreacted residual gas from the first reactor stage and the raw methanol stream from the first reactor stage by condensation.

3. The method according to claim 1, wherein a portion of the pressure-increased residual gas stream is diverted and fed to the synthesis gas reactor arrangement, wherein the diverted portion of the pressure-increased residual gas stream is fed to the energy carrier stream.

4. The method according to claim 1, wherein the methanol reactor arrangement has a plurality of reactor stages for the synthesis of methanol which are operationally connected in series, wherein the recycle compressor is operationally disposed between two reactor stages, wherein by the methanol separation device, a respective unreacted residual gas is obtained from each of the plurality of reactor stages.

5. The method according to claim 4, wherein the H recycle stream is fed to the unreacted residual gas a reactor stage which is operationally downstream of the first reactor stage, wherein the H recycle stream is fed to the recycle compressor together with the residual gas stream for increasing pressure.

6. The method according to claim 4, wherein the residual gas stream is obtained from a reactor stage which is operationally downstream of the first reactor stage, wherein the recycle compressor feeds the pressure-increased residual gas stream to the first reactor stage.

7. The method according to claim 6, wherein the residual gas stream is obtained from a reactor stage of the plurality of reactor stages which is in the last operational position.

8. The method according to claim 1, wherein at least a portion of the recovery stream is diverted from the unreacted residual gas of the first reactor stage, wherein at least a portion of the recovery stream is diverted operationally upstream of the recycle compressor.

9. The method according to claim 8, wherein the recovery stream is fed to the hydrogen recovery arrangement at a feed pressure which is higher than a residual gas pressure at which the residual gas stream is obtained from the methanol reactor arrangement, wherein at least a portion of the recovery stream is diverted out of the residual gas stream operationally downstream of the recycle compressor.

10. The method according to claim 1, wherein the H recycle stream is fed to the synthesis gas stream which has been pressure-increased.

11. The method according to claim 1, characterized in that for obtaining the synthesis gas stream, an oxygen-containing stream is fed to the synthesis gas reactor arrangement, in wherein in the synthesis gas reactor arrangement, the synthesis gas stream is obtained by means of autothermal reforming or a partial oxidation of the carbon-containing energy carrier stream, wherein the oxygen-containing stream is obtained from an air separation device for obtaining a stream of oxygen from ambient air.

12. The method according to claim 1, wherein the H recycle stream is fed to the energy carrier stream, operationally upstream of the synthesis gas reactor arrangement, in that the hydrogen recovery arrangement outputs a purge stream which is discharged for combustion.

13. The method according to claim 1, wherein the H recycle stream has a higher molar proportion of hydrogen than the recovery stream, wherein the H recycle stream has a higher molar proportion of hydrogen than the purge stream.

14. The method according to claim 1, wherein the hydrogen recovery arrangement has a pressure swing adsorption device for obtaining the H recycle stream from the recovery stream.

15. The method according to claim 1, characterized in that the pressure of the unreacted hydrogen of the recovery stream from the first reactor stage up to its feed again into the first reactor stage is increased exactly once along with the unreacted oxides of carbon by means of the recycle compressor.

16. A plant for the synthesis of methanol, with a synthesis gas reactor arrangement for obtaining a synthesis gas stream with hydrogen and oxides of carbon from a carbon-containing energy carrier stream, with a synthesis gas compressor for increasing the pressure of the synthesis gas stream, with a methanol reactor arrangement which has a first reactor stage, with a heat recovery device for recovering heat from the synthesis gas stream, with a hydrogen recovery arrangement and with a recycle compressor, wherein at least a portion of the pressure-increased synthesis gas stream is fed to the first reactor stage for partial conversion into methanol, wherein a residual gas stream with unreacted oxides of carbon is obtained from the methanol reactor arrangement, the residual gas stream being fed to the recycle compressor for increasing the pressure of the residual gas stream, wherein the pressure-increased residual gas stream is fed to the methanol reactor arrangement for partial conversion into methanol, wherein the synthesis gas stream is fed to the heat recovery device and thereafter to the synthesis gas compressor, wherein a recovery stream from an unreacted residual gas from the first reactor stage is fed to the hydrogen recovery arrangement for obtaining a H recycle stream, the H recycle stream having unreacted hydrogen from the unreacted residual gas, the unreacted hydrogen of the H recycle stream being fed again to the first reactor stage for at least partial conversion into methanol, wherein the pressure of at least a portion of the unreacted hydrogen of the H recycle stream from the first reactor stage up to its feed again into the first reactor stage is increased along with the unreacted oxides of carbon by means of the recycle compressor.

* * * * *